United States Patent [19]
Schifftner

[11] Patent Number: 5,861,123
[45] Date of Patent: Jan. 19, 1999

[54] ULTRAVIOLET LIGHT IRRADIATED EBULLATING MASS TRANSFER SYSTEM

[75] Inventor: Kenneth C. Schifftner, Encinitas, Calif.

[73] Assignee: Ceco Filters, Inc., Conshohocken, Pa.

[21] Appl. No.: 638,042

[22] Filed: Apr. 26, 1996

[51] Int. Cl.$^6$ .............................. A61L 2/10; B01J 19/12; B01J 8/42
[52] U.S. Cl. ........................ 422/24; 422/140; 422/186.3; 422/176; 422/187; 250/432 R; 250/455.11
[58] Field of Search .............................. 422/24, 140, 143, 422/186.3, 176, 185, 187; 250/432 R

[56] References Cited

U.S. PATENT DOCUMENTS

| | | | |
|---|---|---|---|
| 2,020,250 | 11/1935 | Stephens et al. | 95/248 |
| 3,138,708 | 6/1964 | Ellner et al. | 210/748 |
| 3,637,342 | 1/1972 | Veloz | 250/436 |
| 3,825,494 | 7/1974 | Call et al. | 210/748 |
| 4,230,571 | 10/1980 | Dadd | 210/760 |
| 4,274,970 | 6/1981 | Beitzel | 210/748 |
| 4,432,914 | 2/1984 | Schifftner | 261/111 |
| 4,728,368 | 3/1988 | Pedziwiatr | 134/1 |
| 4,769,131 | 9/1988 | Noll et al. | 210/85 |
| 4,798,702 | 1/1989 | Tucker | 422/24 |
| 4,941,957 | 7/1990 | Zeff et al. | 204/157.3 |
| 5,063,030 | 11/1991 | Sweetman | 422/189 |
| 5,116,582 | 5/1992 | Cooper et al. | 422/186.3 |
| 5,124,131 | 6/1992 | Wekhof | 422/186.3 |
| 5,238,581 | 8/1993 | Frame et al. | 210/748 |
| 5,258,124 | 11/1993 | Bolton et al. | 210/748 |
| 5,352,359 | 10/1994 | Nagai et al. | 210/192 |
| 5,374,405 | 12/1994 | Firnberg et al. | 422/186.3 |
| 5,635,133 | 6/1997 | Glazman | 422/24 |

FOREIGN PATENT DOCUMENTS

| | | |
|---|---|---|
| 642821 | 9/1994 | European Pat. Off. . |

OTHER PUBLICATIONS

Perry's Chemical Engineers' Handbook, Sixth Edition, Robert H. Perry, Don W. Green, James O. Maloney, pp. 58–75, 1984.

Concise Encyclopedia of Chemical Technology, Kirk–Othmer, pp. 497–499, 1985.

The UV/Oxidation Handbook, Solarchem Environmental Systems, Chapters, 1–5, 1994.

Solarchem Environmental Systems paper entitled, RAYOX®, How to Evaluate and Cost UV/Oxidation Systems, Robert Notarfonzo and Wayne McPhee, Oct. 1993, pp. 1–6.

Fischer & Porter brochure entitled, Ultra Violet Disinfection, Specification Ultra Violet Disinfection Series 70UV6000, Section 28 (1993).

Fischer & Porter brochure entitled, Ultra Violet Disinfection (Packaged Small Systems), Specification Ultra Violet Disinfection Series 70UV3300, Section 28 (1993).

Homogenous Photodegration of Pollutants in Contaminated Water: An Introduction, James R. Bolton and Stephen R. Cater, Chapter 33, pp. 467–490 (undated).

The Solarchem Rayox® Process, UV/Oxidation Systems for Dissolved Organics Destruction—Outshining The Treatment Alternatives, brochure (undated).

Solarchem Environmental Systems paper entitled, Rayox®—UV/Peroxide, Treatment of TCE, PCE, BTEX, Vinyl Chloride, and other Organics, (undated).

*Primary Examiner*—Lila Feisee
*Assistant Examiner*—Michael Pak
*Attorney, Agent, or Firm*—Seidel Gonda Lavorgna & Monaco, PC

[57] ABSTRACT

A mass transfer system for decontaminating a contaminated liquid or gas stream. The system includes a container with a liquid inlet, a liquid outlet, a gas inlet and a gas outlet. The container is adapted to channel a liquid stream from the liquid inlet to the liquid outlet. The vessel is also adapted to channel a gas stream from the gas inlet to the gas outlet. At least one grid is mounted within the container and is positioned within the gas and liquid streams. The grid has a plurality of apertures formed therein which are adapted to disperse the gas flow as it passes through the grid. The dispersion of the gas flow generates a fluidized bed within the container. The grid is preferably parabolic in shape. A light assembly is mounted on the container and has a light emitting unit positioned so as to emit light into the container. The light irradiates at least one of the streams flowing therein. The configuration of the system is designed to cause the mixture of the gas stream and liquid streams to become turbulent, thereby increasing the liquid surface area. The light emitting unit is positioned so as to irradiate the two turbulent fluid flows so as to catalyze a chemical reaction. In one embodiment, an oxidant is added to one of the streams which, when irradiated by the ultraviolet light, produces hydroxyl radicals which chemically react with the contaminants in the stream.

33 Claims, 5 Drawing Sheets

ULTRAVIOLET LIGHT IRRADIATED EBULLATING MASS TRANSFER SYSTEM

FIELD OF THE INVENTION

The present invention relates to a mass transfer system for removal of particulate matter entrained in a gas or liquid stream and, more particularly, to a system which irradiates and scrubs a gas of liquid stream for eliminating undesirable contaminates.

BACKGROUND OF THE INVENTION

A heightened awareness of the effects that chemical by-products have on the environment has led to more stringent governmental regulations on virtually all chemical processes. Many of these regulations are directed to limiting levels of toxics and related chemicals which can be discharged into the environment. For example, the process gases in pulp and paper manufacture include trace levels of methanol and AOX (absorbable organic halogens). These contaminants travel with the process gases and may escape into the atmosphere or into the end product if not removed prior to discharge.

There are many methods for removing gaseous contaminates and particulate matter from gas or liquid streams. One method which is finding increased interest is known as scrubbing. Scrubbing involves the mixing of a process gas or vapor with a scrubbing liquid in a vessel. The mixing of the two constituents is designed to dislodge entrained particulate matter or to remove soluble gases from the gas or vapor stream. One method for scrubbing utilizes a tray or grid through which the gas or vapor stream and the liquid stream are passed. The grid consists of a plurality of apertures. As the gas/vapor stream passes through the grid and meets with the liquid stream, ebullition or bubbling of the liquid occurs on one side of the grid. The bubbling of the two streams forms as a fluidized bed. As the process gas bubbles pass through the fluidized bed the bubbles burst creating small droplets that impact into the contaminate particles and create a large surface area for gas absorption. Alternately, if the liquid and/or gas stream is mixed with a chemical scrubbing agent, reaction and neutralization of entrained contaminate gases may occur.

Conventional scrubbing processes are designed to provide a continuous flow of gas and liquid streams. That is, the liquid and gas feed stock streams are continuously introduced into a contact vessel, and the resulting gas and liquid product streams are continuously withdrawn. Countercurrent flow of the gas and liquid streams is the most common flow pattern used in conventional scrubbers. The liquid stream is introduced at or near the top of the vessel and withdrawn at the bottom. The gas stream is fed in at or near the bottom of the vessel and withdrawn at the top. Concurrent flow type scrubbers channel both streams through the vessel in the same direction.

The grids or trays are mounted at one or more locations within the vessel so as to insure that the desired degree of contact between the gas and liquid occurs. The desired degree and duration of contact between the streams is dependent on many considerations, such as the desired quality (purity) and quantity (yield) needed. It may also be desirable to minimize the pressure drop of the gas stream through the contact or scrubbing vessel. The configuration of the apparatus is also an important feature inasmuch as the preferred vessel is small, simple and relatively easy to maintain.

U.S. Pat. No. 4,432,914, incorporated herein by reference, discloses a catenary grid scrubber which is effective in removing particulate matter and soluble gases from a process gas stream. The scrubber includes a parabolic or contoured grid designed to effectively and efficiently control the rate of gas and liquid interaction so as to maximize the capture or solubility of the entrained contaminates.

To date, scrubber effectiveness has been limited to removing particulate matter or inducing solubility of entrained gases. Alternate systems have been developed to remove insoluble contaminate gases or microscopic particulate (e.g., bacteria). One such system uses ultraviolet light to destroy or chemically convert the contaminate. Ultraviolet (UV) light systems operate by directing a high intensity UV light at a liquid steam that includes a process chemical (usually an oxidant) containing the contaminant. The properties of the UV light produce a catalytic reaction within the stream which eliminates the contaminant or converts it to a more favorable chemical composition which may be subsequently removed.

The primary deficiency with UV light systems is that they are surface area dependent. That is, the UV light cannot deeply penetrate into a liquid stream for irradiating the contaminants. UV light systems, therefore, must channel the liquid stream through thin tubes during UV light irradiation. This severely limits the quantity of irradiated product that can be produced using a UV light system. In order to increase the amount of surface area of liquid irradiated, conventional systems utilize a plurality of thin tubes, each with a suitable UV light source. UV light systems are also not effective in removing large particulate matter from gas streams.

However, as stricter government regulations are imposed on the pulp and paper, electronics and chemical processing industry, these conventional methods for cleaning gas and/or liquid streams are becoming less and less effective. For example, the government has recently proposed stricter rules on the amount and type of emissions allowed in a pulp bleaching operation. These rules propose the elimination of methanol from the pulp bleach plant scrubber exhaust. Conventional scrubbers cannot effectively remove methanol from a process stream. Conventional UV light systems are capable of removing the methanol from a liquid stream but only on a small scale.

Criticism has also developed over the use of chlorine based biocides in cooling tower water disinfection and algae control. In order to effectively disinfect water, conventional scrubbing devices would require the use of non-chlorine additives. UV light systems can be utilized but, due to the small surface area required for effectively catalyzing the contaminates, the amount of product stream cleansed is limited.

A need therefore exists for an improved system that effectively and efficiently removes particulate matter and/or soluble gaseous matter from a process stream, while producing a large liquid surface area that can be irradiated with UV light for the destruction of the absorbed organic compounds.

SUMMARY OF THE INVENTION

The present invention is directed to a mass transfer system for decontaminating a contaminated liquid or gas stream. The system includes a container with a liquid inlet, a liquid outlet, a gas inlet and a gas outlet. The container is adapted to channel a liquid stream from the liquid inlet to the liquid outlet. The vessel is also adapted to channel a gas stream from the gas inlet to the gas outlet.

At least one grid is mounted within the container and is positioned within the gas and liquid streams. The grid has a plurality of apertures formed therein which are adapted to disperse the gas flow as it passes through the grid. The dispersion of the gas flow generates a two fluid, turbulent fluidized bed within the container. The grid is preferably parabolic in shape.

A light assembly is mounted on the container and has a light emitting unit positioned so as to emit light into the container. The light irradiates at least one of the fluidized, turbulent streams flowing therein.

The configuration of the system is designed to cause the mixture of the gas stream and liquid streams to become turbulent thereby exposing increased liquid surface area for irradiation. The light emitting unit is positioned so as to irradiate the turbulent gas stream flow so as to produce a chemical reaction.

In one embodiment, an oxidant is added to one of the streams which, when irradiated by the ultraviolet light, produces hydroxyl radicals which chemically react with the contaminants in the stream.

Methods for decontamination of a stream are also disclosed and include the steps of supplying a contaminated stream and a second stream. One of the streams is a liquid stream and the other is a gas stream. Intermixing the contaminated stream and the second stream by passing the streams through the grids, the intermixing of the streams producing ebullition of the mixed streams and forming a fluidized bed. The fluidized bed is then irradiated with ultraviolet light to cause decontamination of the contaminated steam.

The foregoing and other features and advantages of the present invention will become more apparent in light of the following detailed description of the preferred embodiments thereof, as illustrated in the accompanying figures.

BRIEF DESCRIPTION OF THE DRAWINGS

For the purpose of illustrating the invention, there is shown in the drawings a form which is presently preferred; it being understood, however, that this invention is not limited to the precise arrangements and instrumentalities shown.

DESCRIPTION OF THE PREFERRED EMBODIMENTS

While the invention will be described in connection with one or more preferred embodiments, it will be understood that it is not intended to limit the invention to any particular embodiment. On the contrary, it is intended to cover all alternatives, modifications and equivalents as may be included within the spirit and scope of the invention as defined by the appended claims.

Certain terminology is used herein for convenience only and is not be taken as a limitation on the invention. For example, the process stream is described as a water or liquid stream. This description, however, is also intended to encompass an embodiment wherein the process stream is a vapor or gas stream. Similarly, the light source is described as an ultraviolet light. However, other wavelengths of light are intended to be encompassed by the invention.

It is to be understood that the principles of the present invention have broad application to many types of gas-liquid contact devices. For purposes of illustration, however, the following description will elaborate primarily on a system for removing contaminants from an aqueous stream, such as cooling tower water, with a mass transfer system (e.g., scrubber).

Figure 1:
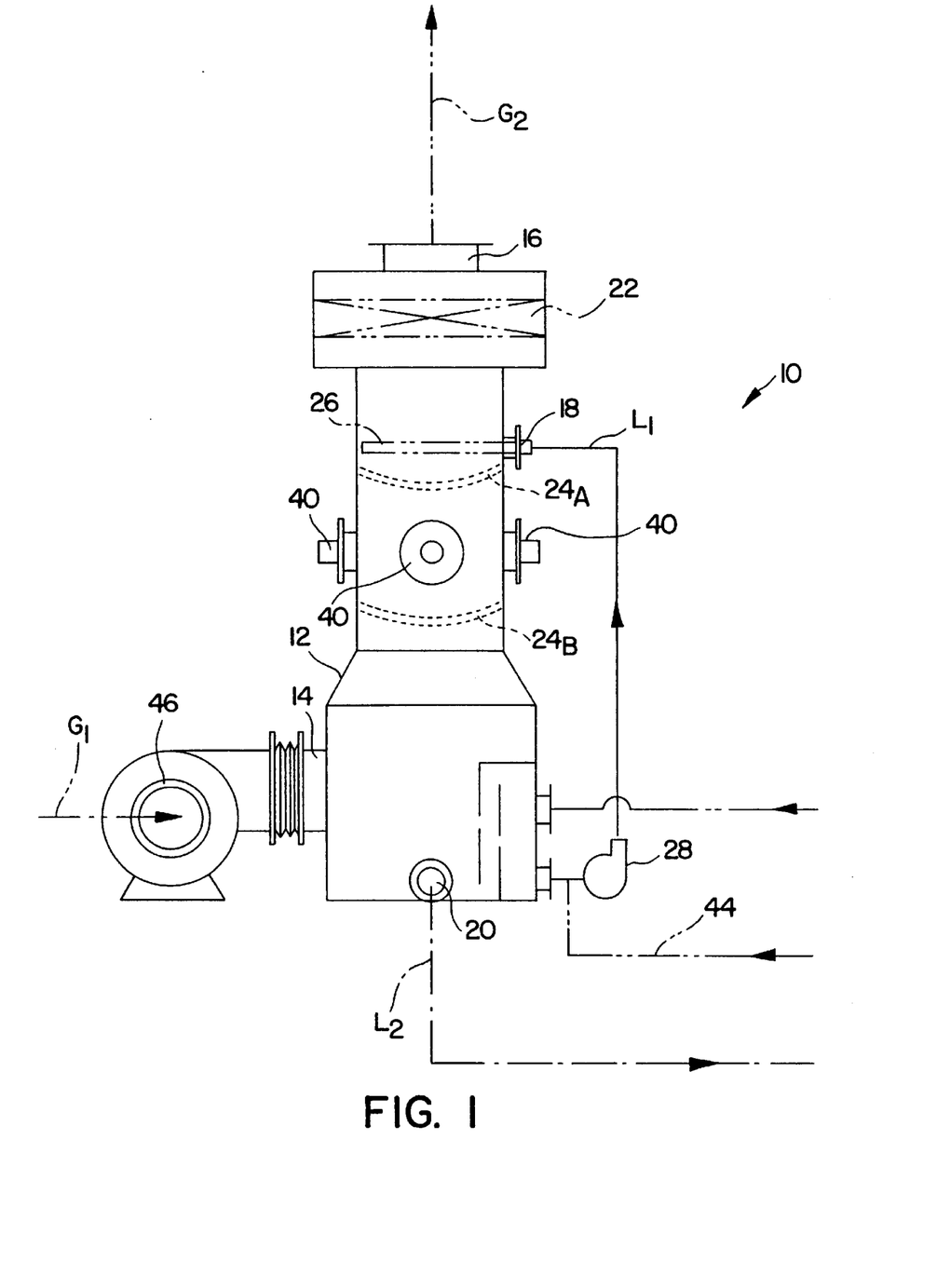
FIG. 1 is a side view of a mass transfer system according to the present invention.

FIG. 1 illustrates one embodiment of the ultraviolet light irradiated ebullating mass transfer system 10 for use in decontaminating cooling tower water. The mass transfer system 10 includes a contact container or vessel 12 having a gas inlet 14 and outlet 16 and a liquid inlet 18 and outlet 20. The illustrated contact vessel 12 is of the counter-current type and, accordingly, a flow of gas (designated by flow lines G1 and G2) from the gas inlet 14 to the gas outlet 16 runs opposite to a flow of liquid (designated by flow lines L1 and L2) from the liquid inlet 18 and liquid outlet 20. The two flows contact one another within the confines of the vessel 12.

A droplet eliminator 22 is positioned within the flow path of the gas stream at a location downstream from the liquid inlet 18. The droplet eliminator 22 is conventional in the art and is not critical to the invention.

Suspended within the vessel 12 are one or more grids 24 (shown in phantom). The grids 24 are positioned within the gas stream between the liquid inlet 18 and the gas inlet 14. The grids 24 are preferably removably attached to the sides of the vessel 12 by a suitable attachment means so as to permit the grid 24 to be removed for cleaning or replacement. The grids 24 are also preferably oriented such that they are essentially perpendicular to the direction of gas flow. In the illustrated embodiment, there are two grids $24_A$ and $24_B$ spaced apart from one another along the axis of gas flow. Additional grids 24 may be incorporated into the vessel configuration if desired.

The grids 24 are preferably contoured with a shallow, parabolic shape. The parabolic shape of the grids 24 is designed to control the velocity pressure profile of the gas flow. When gases pass through a duct, a velocity pressure profile results which appears to approximate a shallow parabola. The velocity pressure is maximum in the center of the vessel 12 and decreases to nearly zero at the vessel wall. As the gas velocity increases (e.g., above 10–15 feet/second) the velocity pressure profile becomes more pronounced.

As discussed in U.S. Pat. No. 4,432,914, the rate of absorption, impaction or interception between the gas and liquid streams varies across the diameter of the vessel. By incorporating an appropriately shaped grid 24 which is approximately the inverse of the velocity pressure profile (i.e., mirror image) of the gas flow in the vessel 12, the effects of the velocity pressure on the rate of absorption can be largely cancelled out. That is, the shape of the grid 24 operates to even the velocity pressure profile of the gas flow across the diameter of the vessel 12. The even distribution of the gas flow provides for better interaction and absorption with the liquid stream and results in increased efficiency.

The grid 24 can be made of a variety of materials provided the overall strength of the grid 24 can sustain the applied loads. Preferably the material is flexible, thus allowing the grid 24 to be removed and flexed to facilitate cleaning. However, a rigid grid may be utilized if cleaning is not a concern.

The net open area of the grid 24 is selected to accommodate various conditions. For example, grids with small amount of open area may be utilized where conservation of liquid is desired or to increase the grids structural strength. Grids 24 with a large amount of open area are useful for reducing energy demands, or to facilitate the drainage of liquids containing higher percentages of solids. Those skilled in the art would readily be capable of selecting a suitable grid configuration for a prescribed operation.

The shape of the catenary grid 24 can be configured so as to provide an energy equilibrium condition between the liquid and the gas streams. As a result, the liquid introduced to the top of the grid 24 will remain suspended and will fluidize, but will not initially drain. Since it is desirable to maintain a constant flow of liquid through the vessel 12, it is desirable to create an equilibrium imbalance in favor of the liquid stream. This is achieved by further deepening the shaped grid and introducing a constant supply of scrubbing liquid. The incoming liquid displaces the liquid that has been on the grid in a fluidized state. Liquid replenishment, therefore, can be forced to occur and can be controlled to maximize the efficiency of the system for different liquid and gas streams.

The preferred distance between the two or more grids 24 will vary depending on various parameters such as gas velocity, gas density and grid open area. However, the primary determining factor in the spacing of the grids 24 is the creation of a turbulent zone between the grids 24. If the grids are too far apart, the flowing gas may begin to establish an unstable velocity pressure profile. It has been determined that spacings between approximately eighteen and twenty-four inches result in improved performance. Generally, if gas density or velocity decreases, or grid open area increase, the spacing between the grids decreases.

Mounted above at least one of the grids 24 is a header 26 which functions as a means for dispensing a stream of liquid into the vessel 12. Various types of header configurations can be employed in the present invention (e.g., spray, free flow, tangential, weirbox, etc.). The most common method is a horizontally oriented pipe with holes spaced along its length. The header 26 is connected to a liquid supply (not shown) which in the present embodiment is tower water. One or more nozzles (indicated by numeral 27 in FIG. 2) may be attached to the header 26 to dispense the liquid in droplet form across the breadth of the vessel 12 and onto the upper surface of the top grid 22$_A$. A pump 28 is positioned within the liquid stream between the liquid supply and the liquid inlet 18 and functions to pump the liquid from the source to the header 26. In the present embodiment, the header 26 is positioned so as to dispense a liquid stream onto the concave side of the upper grid 22$_A$. Preferably the liquid is dispensed at a pressure between about two psig and about five psig although other pressures are well within the scope of the invention.

Figure 2:
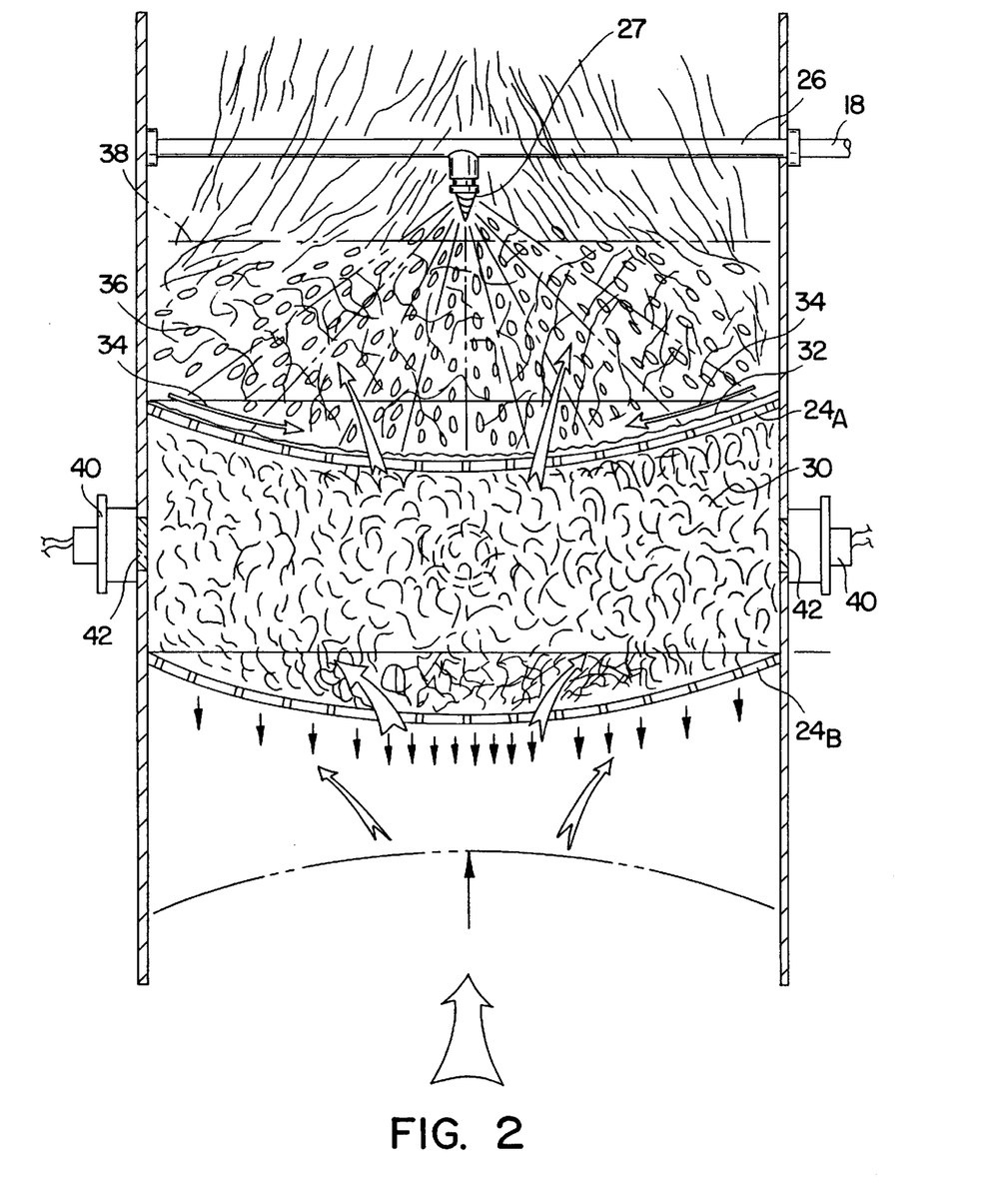
FIG. 2 is a partial section view of the mass transfer system according to the present invention illustrating a fluidized bed and turbulent zone.

FIG. 2 illustrates the flow patterns of the liquid and gas streams within the vessel 12. The liquid is shown being dispersed from a nozzle 27 onto the upper grid 24$_A$.

As the gas passes through the lower catenary shaped grid 24$_B$, a zone of high turbulence and random flow paths (indicated by the numeral 30) are created between the upper and lower grids 24$_A$, 24$_B$. The lower grid 24$_A$ also acts as an energy dissipator, resulting in a reduced energy level of the gases in the turbulent zone 30. As the turbulent gases pass through the upper grid 24$_A$ the interaction of the turbulent gases with the liquid stream forms a layer 32 on the top surface of the upper grid 24$_A$. The shape of the catenary grid causes the layer 32 to move toward the center of the vessel as indicated by arrows 34.

A fluidized bed or zone 36 forms above the layer on the upper grid 24$_A$. The fluidized zone is generated when the turbulent gases pass through the grid and the liquid layer 32. Ebullition or bubbling of the combination occurs on and above the top surface of the upper grid 24$_A$. The bubbling of the combination forms the fluidized zone and contains randomly dispersed, high surface area droplets of liquid and gases which efficiently and effectively interact with one another. The bubbles burst as they pass through the fluidized bed providing targets for the impaction of any entrained contaminate particles. Additionally, the dispersement of the liquid and gas results in improved absorptive characteristics.

The height 38 of the fluidized zone 36 will be a function of the droplet size and the velocity of the gas. The higher the fluidized zone, the greater the gas absorption and particulate removal. For a properly dished grid, the top surface 38 of the zone will be substantially flat as shown. With a shallower dish configuration, the center area of the top surface 38 rises up higher than the area near the vessel sides reflecting less dispersement of the gases towards the sidewall and less effective interaction of the liquid and gas streams. If the depth of the grid is too shallow, flow through of the gases may occur in the center of the vessel.

Because of the energy imbalance in favor of the liquid, the liquid droplets in the fluidized zone 36 will eventually collect and drain through the upper grid 24$_A$ into the turbulent zone 30 where additional reaction with the gas takes place. The liquid will then drain through the lower grid 24$_B$ and collect at the bottom of the vessel 12 where it is channeled out through the liquid outlet 20. The amount of time that a droplet of liquid remains in the fluidized zone will vary depending on many factors, and has been experimentally determined to be as long as 3 to 4 seconds.

The above system effectively and efficiently removes entrained particulate matter and/or soluble gases. If desired, an additive may be incorporated into either the gas or liquid streams to assist in removing or catalyzing entrained contaminants.

Referring back to FIG. 1, the present invention further enhances the decontaminating capabilities of the above system by incorporating lamp assemblies 40 into the vessel 12. As discussed above, ultraviolet light (UV) can be utilized as a catalyst to assist in destroying organics in liquids. More specifically, when UV light is brought into contact with a strong oxidant, such as hydrogen peroxide, the combination forms hydroxyl radicals that destroy benzene ring bonds in dioxins and cyclic toxics. This results in the oxidation of the toxics in a stream into less hazardous compounds. The UV light is also capable of killing bacteria in water, thereby making the water safer to drink. The UV light can also kill bacteria in cooling tower water that could otherwise lead to respiratory diseases (such as Legionnaire disease).

The lamp assemblies 40 are mounted to the vessel 12 at predetermined locations and configured so as to direct light inward for irradiating the gas and liquid streams. In the illustrated embodiment, the light assemblies are mounted at 90 degree increments around the periphery of the vessel 12 in order to completely irradiate the passing streams. The positions of the light assemblies would, of course, be varied depending on the vessel configuration and/or the light assembly design. The light assembly 40 includes a light emitting unit (not shown) which is connected to a power source. In a preferred embodiment the light emitting unit is an ultraviolet light having a wavelength between about 200 and 500 nanometers. Wavelengths of 250 to 270 nanometers are the most effective for pathogenic microorganisms. The ultraviolet light is preferably a medium-pressure mercury lamp having a power between one kilowatt and 30 kilowatts. More preferably, the power is between 15 and 30 kilowatts. A smaller wattage lamp may be suitable (e.g., 1–5 kilowatts). However, a larger number of lamps may then be required to completely irradiate the passing stream. The preferred voltage is between 1,000 and 3,000 volts. The light assembly 40 is preferably attached to the vessel 12 so as to permit access to the light emitting unit for removal and/or maintenance. The light assembly 40 is conventional in the art and does not need to be discussed in any further detail.

Located between each light assembly 40 and the streams of gas and liquid within the vessel 12 is a shield 42. Referring to FIG. 2, the shield 42 is shown mounted within the side wall of the vessel 12 and defines a window through which the UV light passes to irradiate the gas and liquid flows. The shield 42 is made of a UV-transparent material such as quartz. Standard glass absorbs UV light and, therefore, is not preferred.

The shield 42 can be removably mounted to the vessel 12 thereby providing for easy cleaning and maintenance. A wiper assembly (not shown) may be mounted in the interior of the vessel in the vicinity of the shield 42 to permit cleaning of the interior surface of the shield before, during or after processing of the flows without having to access the interior of the vessel 12. Wiper assemblies are well known in the art and, therefore, a detailed discussion is not needed. Mounting the light assemblies 40 on the exterior of the vessel permits easy repair and replacement of the UV lights.

Figure 3:
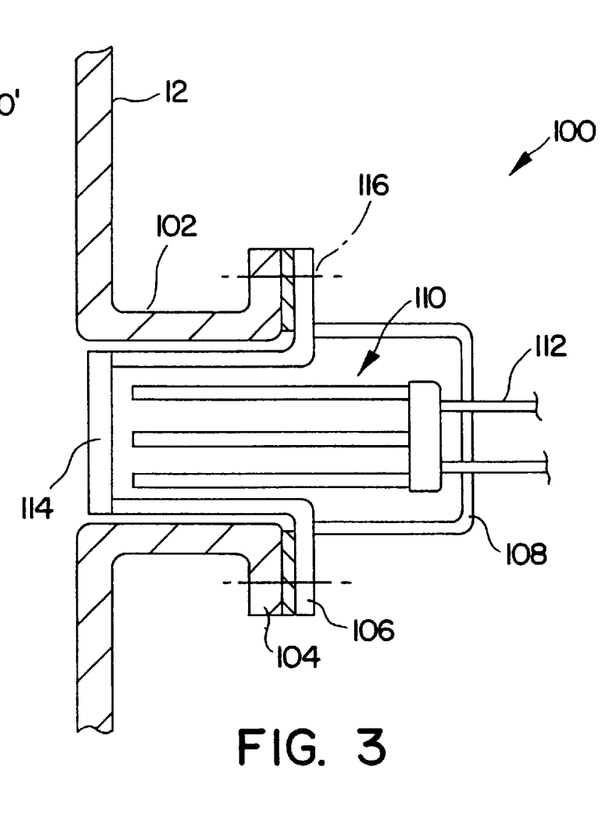
FIG. 3 shows one embodiment of an ultraviolet light assembly for use in the present invention.

Referring to FIG. 3, one preferred mounting arrangement and ultraviolet light assembly 100 is shown. In this embodiment, a tower fitting 102 is formed on the exterior of the vessel 12. The fitting 102 can be of any desired shape. In the illustrated embodiment, the fitting 102 is cylindrical in shape and welded to the vessel 12. The fitting 102 has a mounting flange 104 formed around a peripheral edge.

Figure 3A:
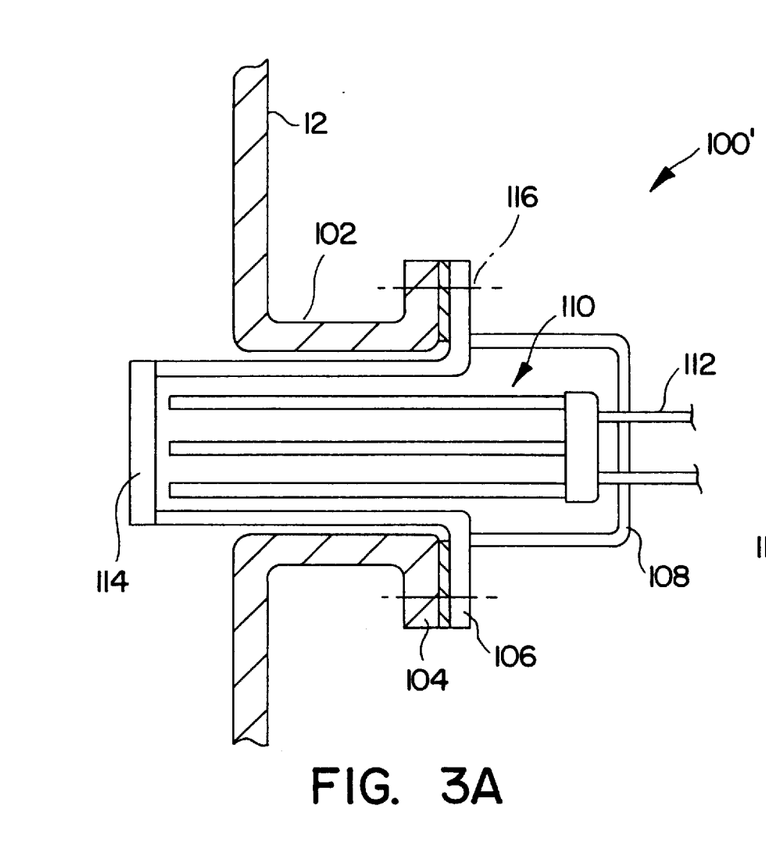
FIG. 3A shows a modification of the embodiment of an ultraviolet light assembly shown in FIG. 3.

The ultraviolet light assembly 100 includes a housing 106 onto which is mounted a cover 108. Located within the cover 108 is an ultraviolet light array 110. The light array 110 has electrical contacts 112 which preferably extend out of the cover 108. The contacts 112 are electrically connected to a power source (not shown) for energizing the light array 110. The housing 106 has a quartz window 114 attached to it at an opposite end from the cover 110. The housing 106 is preferably attached to the mounting flange 104 by at least one removable fastener 116 so as to permit access to the interior of the housing 106. The cover 108 is also preferably removable so as to permit access to the ultraviolet light array 110. The small size of this light assembly 100 permits a plurality of the ultraviolet light assemblies 100 to be mounted around the periphery of the vessel 12 for irradiating the fluidized bed within. FIG. 3A illustrates a variation of this embodiment of the light assembly 100' wherein the light array 110 extends into the interior of the vessel.

Figure 4:
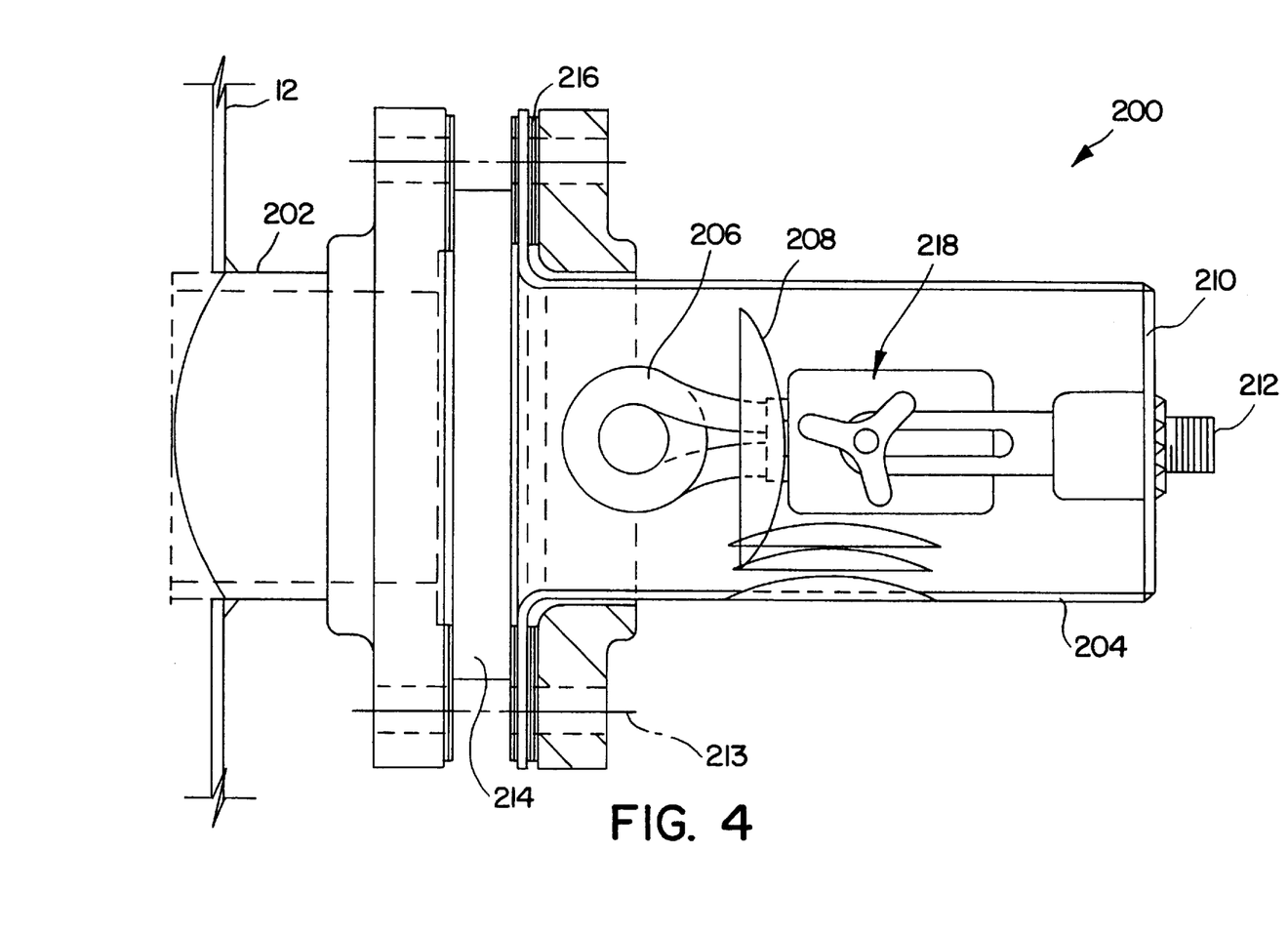
FIG. 4 shows another embodiment of an ultraviolet light assembly for use in the present invention.

FIG. 4 illustrates a second preferred ultraviolet light assembly 200. In this embodiment, a tower fitting 202, similar to the fitting described above, extends out from the vessel periphery. The ultraviolet light assembly 200 includes a housing 204 within which is mounted an ultraviolet light tube 206. A reflector 208 is positioned between the light tube 206 and a back wall 210 of the housing 204. As with the previous embodiment, electrical contacts 212 extend out of the housing 204. The housing 204 is mounted to the tower fitting 202 through one or more fasteners 213. Preferably, a quartz window 214 is mounted between the housing 204 and the tower fitting 202. Gaskets 216 may be incorporated to prevent leakage of the ultraviolet light from the assembly. An adjustment mechanism 218 may be incorporated to vary the position of the UV light tube 206.

Figure 5:
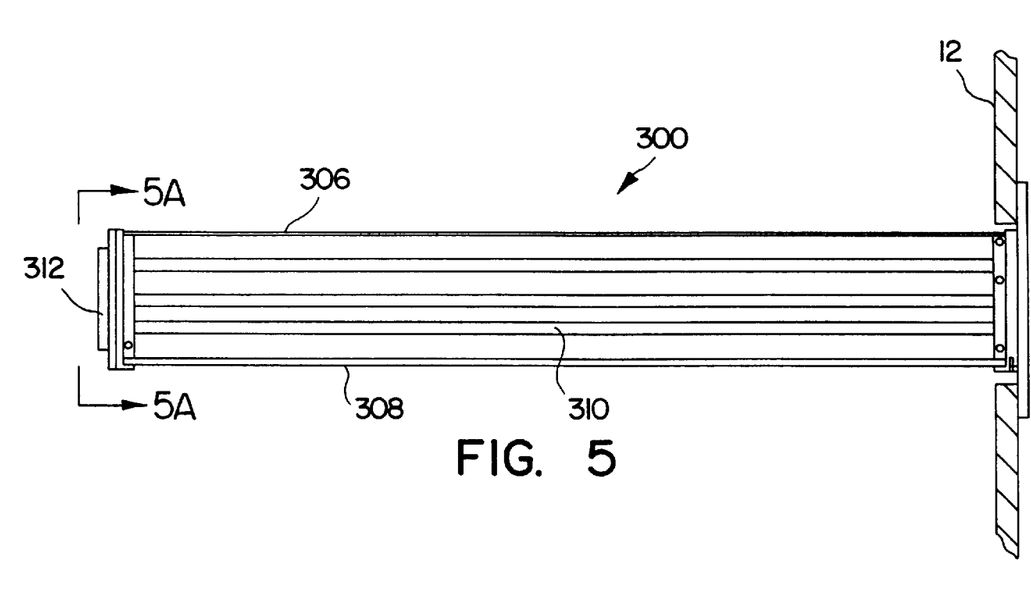
FIGS. 5 and 5A shows yet another embodiment of an ultraviolet light assembly for use in the present invention.
Figure 5A:
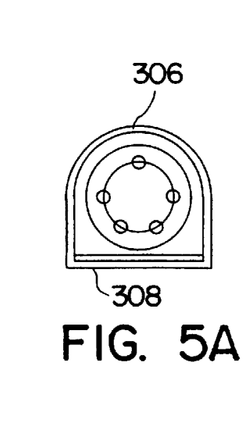

FIGS. 5 and 5A illustrates yet another light assembly 300. In this embodiment, the light assembly is designed to extend across at least a portion of the interior of the vessel 12. The light assembly 300 includes an mounting flange 302 formed on a housing 304. The mounting flange is configured to attach to the side of the vessel 12. The housing 304 extends through an opening in the vessel 12 and may attach to a mount on the opposite side of the vessel. The housing 12 includes a semi-cylindrical shaped reflector 306 and a quartz window 308. The quartz window preferably closes off the open side of the is reflector 306 so as to form an enclosure. An ultraviolet light array 310 (i.e., one or more ultraviolet lamps) is located within the enclosure. An end cap 312 closes off the open end of the housing.

This embodiment of the light assembly 300 is preferably located across the center to the vessel so as to permit the ultraviolet light to completely irradiate the passing fluid flow. Alternate light assemblies can be substituted for any of the disclosed embodiments, and are well within the purview of the claims.

The vessel 12 is preferably made from stainless steel, corrosion resistant alloy steel, or fiberglass reinforced plastic with a UV inhibitor on the inside surface. The grids are preferably made from corrosion resistant alloy steel, titanium, or fiberglass reinforced plastic.

In order for the UV light to initiate degradation of the toxics within the gas and/or liquid streams, the UV light must penetrate into the streams. Conventional UV light emitters reduce the diameter of the liquid flowing in quartz tubes in order to permit the light to contact oxidants contained within the flow. The present invention does not reduce the diameter of the liquid flow but, instead, directs the light into the dispersed turbulent zone formed between the grids 24. In the illustrated embodiment, the UV lights are mounted so as to direct light between the upper and lower grids $24_A$, $24_B$ into the zone of high turbulence 30. The gas flow in the turbulent zone 30 flows upward in an extremely random manner lacking any distinct pressure profile. This upward flow of dispersed gas mixes with the liquid flowing down from the upper grid $24_A$ causing the liquid flow to disperse and separate in a turbulent manner. The UV light is focused directly into this random and turbulent mixing of the gas and liquid streams. The dispersed nature of the mixture and constantly renewed liquid surface area, in combination with the continuous turbulence of the flows, maximizes the amount of UV light that penetrates into the gas and liquid streams. The result is more efficient use of the UV light source.

In an alternate configuration (not shown), the light assembly 40 is mounted on a lance within the center of the vessel 12. The light assembly emits UV light outward toward the walls of the vessel so as to irradiate the streams as they flow past the light assembly 40.

If only a single grid 24 is utilized in the vessel 12, then it is preferred that the light assembly 40 is mounted above or below the grid 24. By mounting the light assembly directly under the grid 24, the UV light will irradiate the liquid flow as it is dispersed by the upward flowing gases. Alternately, the light assembly 40 can be mounted above the grid so as to irradiate the fluidized zone 36 where the dispersed nature of the ebullating liquid and gas mixture allows for maximum UV penetration. This later embodiment may also be used in the two grid embodiment if mounting between the grids is not possible or not desired. In either of the above mounting arrangements, the UV light irradiates the liquid stream as it descends and subsequently rises (due to the ebullition).

The gas stream in this mass transfer system is also irradiated by the UV light as it rises. Accordingly, any toxics contained within the gas flow that may have been transferred by contact with the liquid stream will be irradiated.

In order to enhance the effect of the UV light on the material streams, a flow of oxidant is preferably interjected into at least one of the streams. In the embodiment illustrated in FIG. 1, the flow of oxidant (designated by line 44) is fed into the liquid stream. The mixture is then channeled into the pump 28 which directs the flow to the liquid inlet 18. The oxidant flows with the liquid into the vessel 12 and mixes with the gas stream in the fluidized zone 36 and the turbulent zone 30. Upon interaction with UV light and or the gas stream, the free radicals are created which chemically react with the contaminants in the gas and/or liquid streams. The dispersement and random flow patterns within the turbulent zone 30 and fluidized zone 36 provide a high degree of mixing of the oxidant and liquid/gas streams. Some prior art systems do not achieve a thorough mixing of the oxidant and liquid/gas streams, thus requiring the addition of substantially more oxidant and/or UV material into the flow. This can become quite expensive and it still does not guarantee even mixing of the combination. The inherent turbulent behavior of the streams within the turbulent zone 30 and the fluidized zone 36 provides complete mixing of the oxidant with the streams.

In one preferred embodiment, the oxidant is hydrogen peroxide ($H_2O_2$). When hydrogen peroxide comes into contact with UV light, hydroxyl radicals are produced that attack the UV unsaturated bonds in dioxins and cyclic toxics forming less hazardous compounds.

One use for the above system is in the treatment of water containing halogenated contaminants, such as chlorinated organic molecules (e.g., trichloroethylene, vinylidene chloride and vinyl chloride). A supply of water is channeled to the vessel and mixed with hydrogen peroxide (or other suitable oxidant). The liquid combination is then channeled into the vessel 12 and dispersed onto the upper grid $24_A$ by the nozzle 27. Concomitantly, a flow of air is pumped into the vessel by a fan 46. The flow of air travels up through the lower grid $24_B$ forming the turbulent zone 30. The liquid collects on the top surface of the upper grid $24_A$ where it comes into contact with the flow of air. The ebullition of the liquid (water/hydrogen peroxide combination) and air forms the fluidized bed 36. The liquid eventually drains through the upper grid $24_A$ into the turbulent zone 30 where it interacts with the turbulent air flows. UV lights are arranged around the perimeter of the vessel so as to completely irradiate the water, hydrogen peroxide, and air combination thereby producing hydroxyl radicals. The hydroxyl radicals that are formed attack the halogenated compounds in the stream and chemically convert it to a more favorable substance, such as carbon dioxide and water. The UV light also operates to kill bacteria within the water.

The air eventually passes upward through the fluidized bed, past the droplet eliminator 22, and out of the vessel 12. The air can be recirculated if desired to further clean the water supply. The decontaminated water eventually drains down to the liquid outlet 20 where it is channeled to a water reservoir. An external recycle tank may be incorporated into the system if the liquid phase oxidation rate is slow. The oxidation rate of peroxide with many benzene ring compounds is relatively slow. A ten minute retention time is typically utilized.

The above configuration can decontaminate up to 30 gallons per minute of contaminated liquid using only approximately 800 cubic feet per minute of air in a vessel only one foot in diameter.

In the above system, the cleaning occurs in an opposite manner than a conventional scrubber. Conventional scrubbers intermix a contaminated gas with a scrubbing liquid to produce cleaning of the contaminated gas. The ebullition of the combination results in the transfer of the contaminants from the gas to the liquid. In the above cleaning system, a contaminated liquid is cleaned by interaction with a flow of clean air.

An alternate use for the above system is in the removal volatile organic carbons, odors, and soluble organics from a gas or air flow. In this embodiment, a liquid stream operates in combination with UV light and an oxidant additive to clean a gas flow in the turbulent zone 30 and the fluidized zone 36. An oxidant-containing liquid efficiently interacts with a gas stream in the fluidized zone 36 and the turbulent zone 30. The interaction between the two flows produces scrubbing of the contaminated gas stream. The zone is irradiated with UV light to further decontaminate the gas stream. The spent liquid/oxidant combination is then reclaimed at the lower end of the vessel 12 for recycling.

The aforementioned embodiment provides a novel system for decontaminating a gas, such as air, to remove volatile organic components, and eliminate odors. This system is also useful in the elimination of phenols and formaldehyde, and the oxidation of ethanol from a fermentation process.

Another use for the present system is the removal of methanol from pulp mill bleach plant emissions. As discussed above, pulp bleach plant effluents contain trace amounts of methanol. To date it has been difficult and expensive to remove the methanol from the effluent. The present invention provides an inexpensive system for removing methanol in an effluent stream by mixing an oxidant into the effluent, subjecting the combination to a gaseous flow, such as air, and then irradiating the flows to oxidize the methanol.

In the above embodiments the additive (e.g., oxidant) has been incorporated into the liquid stream. However, it is also contemplated that the additive may be incorporated instead into the gas stream. Since the gas will typically absorb only a minimal amount of UV light, it will not adversely effect the irradiation of the liquid stream. It is also possible to incorporate additives into both the liquid and gas stream if desired. Also, since many pulp mills currently use hydrogen peroxide in their bleaching sequence, additional peroxide may not be necessary.

The present invention provides a system for decontaminating a contaminated stream with substantially no backmixing of the decontaminated stream with the contaminated stream. That is, the contaminated stream generally flows in a continual forward direction through the vessel.

Although the invention has been described and illustrated with respect to the exemplary embodiments thereof, it should be understood by those skilled in the art that the foregoing and various other changes, omissions and additions may be made therein and thereto, without parting from the spirit and scope of the present invention.

I claim:

1. A mass transfer system for decontaminating a liquid or gas contaminated stream, the system comprising:

a vessel having a liquid inlet, a liquid outlet, a gas inlet and a gas outlet, the vessel adapted to channel a liquid stream from the liquid inlet to the liquid outlet and adapted to channel a gas stream from the gas inlet to the gas outlet;

at least one grid mounted within the vessel and adapted to be positioned within the gas and liquid streams, the grid having a plurality of apertures formed therein adapted to disperse the gas flow as it passes through the grid so as to generate a fluidized bed of the intermixing gas and liquid streams within the vessel; and a light assembly mounted on the vessel and having an ultraviolet light emitting unit positioned so as to emit ultraviolet light into the vessel and irradiate the intermixing streams in the fluidized bed.

2. A mass transfer system according to claim 1 wherein the light assembly is mounted to the vessel so as to cause the light emitting unit to irradiate the fluidized bed.

3. A mass transfer system according to claim 1 wherein the grid causes the gas stream flow to become turbulent and wherein the light emitting unit is positioned so as to irradiate the turbulent gas stream flow.

4. A mass transfer system according to claim 1 wherein the grid has a parabolic shape.

5. A mass transfer system according to claim 4 wherein the liquid stream is dispersed on the concave side of the grid.

6. A mass transfer system according to claim 1 comprising two grids spaced apart from one another, and wherein the light assembly is mounted to the vessel between the grids so that the light emitting unit irradiates at least a portion of the volume between the grids.

7. A mass transfer system according to claim 1 further comprising a nozzle in communication with the liquid inlet for dispersing the liquid in the vessel.

8. A mass transfer system according to claim 1 wherein the contaminated stream is the liquid stream.

9. A mass transfer system according to claim 1 wherein the contaminated stream is the gas stream.

10. A mass transfer system according to claim 1 further comprising means for introducing an additive into at least one of the streams.

11. A system for decontaminating a contaminated stream, the system comprising:

a container having first and second inlets and first and second outlets, the first inlet in communication with the first outlet and adapted for passing a contaminated stream through the container, the second inlet in communication with the second outlet and adapted to pass a second stream through the container;

a grid mounted within the container and adapted to scatter at least one of the streams so as to facilitate intermixing of the streams;

an ultraviolet light emitter attached to the vessel and adapted to irradiate the intermixing streams so as to facilitate decontamination of the contaminated stream; and wherein one of the streams is a gas stream and one of the streams is a liquid stream.

12. A decontamination system according to claim 11 wherein the ultraviolet light emitter is positioned adjacent to the grid.

13. A decontamination system according to claim 11 comprising two grids and wherein the ultraviolet light emitter is attached to the container so as to irradiate the streams between the grids.

14. A decontamination system according to claim 13 wherein at least one of the grids is a catenary grid.

15. A decontamination system according to claim 11 comprising a plurality of ultraviolet light emitters attached to the periphery of the container and adapted to illuminate the interior of the container.

16. A decontamination system according to claim 11 wherein the contaminated stream is a liquid and wherein the second stream is a gas.

17. A decontamination system according to claim 16 wherein the contaminated fluid is water and wherein the gas is air.

18. A decontamination system according to claim 11 further comprising means for introducing an additive into at least one of the streams for assisting in decontamination of the contaminated stream.

19. A decontamination system according to claim 18 wherein the contaminated stream is water, the second stream is air, and the additive is an oxidant.

20. A decontamination system according to claim 19 wherein the oxidant is hydrogen peroxide.

21. A method for decontamination a stream comprising the steps of:

supplying a contaminated stream;

supplying a second stream;

channeling the streams to a grid;

intermixing the contaminated stream and the second stream by passing the streams through the grid, the intermixing of the streams producing ebullition of the mixed streams and forming a fluidized bed;

irradiating the fluidized bed with ultraviolet light, the irradiation causing decontamination of the contaminated stream; and wherein one of the streams is a liquid stream and one of the streams is a gas stream.

22. A method for decontaminating a stream according to claim 21 wherein the contaminated stream is channeled toward a first side of the grid, and wherein the second stream is channeled toward the opposite side of the grid.

23. A method for decontaminating a stream according to claim 21 further comprising the step of supplying an additive to at least one of the streams, and wherein the irradiation causes the additive to oxidize.

24. A method for decontaminating a stream comprising the steps of:

directing a contaminated stream in a first direction through a container;

directing a second stream in a second direction through a container, the second direction being substantially opposite from the first direction;

passing the streams in opposite directions through a grid so as to produce intermixing and dispersement of the streams;

irradiating the intermixing streams with ultraviolet light, the irradiation causing decontamination of the contaminated stream; and wherein one of the streams is a liquid stream and one of the streams is a gas stream.

25. A method for decontaminating a stream according to claim 24 further comprising the step of supplying an additive to at least one of the streams, and wherein the irradiation causes the additive to oxidize.

26. A method for decontaminating a stream comprising the steps of:

directing a contaminated stream in a first direction through a container;

directing a second stream in a second direction through a container, the second direction being substantially opposite from the first direction;

forming a fluidized bed by passing the streams in opposite directions through a first grid so as to produce ebullition of the streams;

irradiating a contact zone formed by the intermixing streams with ultraviolet light, the irradiation facilitating decontamination of the contaminated stream; and wherein of one of the streams is a liquid stream and the other stream is a gas.

27. A mass transfer system according to claim 2 wherein the light assembly further includes a housing mounted to the exterior of the vessel, the housing containing the light emitting unit, and a quartz window disposed between the light emitting unit and the interior of the vessel.

28. A mass transfer system according to claim 11 wherein the ultraviolet light source includes a housing mounted to the exterior of the vessel, the housing containing an ultraviolet light, and a quartz window disposed between the light and the interior of the vessel.

29. A decontamination system according to claim 12 wherein the ultraviolet light emitter is mounted to the exterior of the container, the system further comprising a quartz window positioned between the emitter and the interior of the container.

30. A mass transfer system according to claim 2 wherein the light assembly further includes a housing located at least partially within the interior of the vessel, the housing containing the light emitting unit, and having a quartz window attached thereto.

31. A decontamination system according to claim 12 wherein the ultraviolet light emitter is located at least partially within the interior of the vessel, the system further comprising a quartz window positioned between the emitter and at least one of the streams.

32. A mass transfer system according to claim 1 wherein the grid is mounted within the vessel substantially perpendicular to the flow of the streams within the vessel, and the light assembly is mounted on the exterior of the vessel, the ultraviolet light emitting unit emitting ultraviolet light into the vessel through a quartz window formed in the vessel.

33. A mass transfer system according to claim 1 wherein the intermixing of the gas and liquid streams within the fluidized bed causes turbulent flow within the intermixing streams; and wherein the ultraviolet light emitting unit emits ultraviolet light into the vessel in a direction substantially perpendicular to the flow of the streams and into the turbulent flow of the intermixing streams.

* * * * *